(12) United States Patent
Chinea et al.

(10) Patent No.: US 7,767,249 B2
(45) Date of Patent: Aug. 3, 2010

(54) PREPARATION OF NANOPARTICLES

(75) Inventors: Vanessa I. Chinea, Isabela, PR (US);
Kevin Michael Kane, Moca, PR (US);
Orlando Ruiz, Aguadilla, PR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1408 days.

(21) Appl. No.: 11/189,585

(22) Filed: Jul. 25, 2005

(65) Prior Publication Data

US 2005/0260274 A1    Nov. 24, 2005

Related U.S. Application Data

(60) Continuation-in-part of application No. 10/801,379, filed on Mar. 15, 2004, now abandoned, and a continuation-in-part of application No. 10/801,380, filed on Mar. 15, 2004, now abandoned, and a continuation-in-part of application No. 10/801,381, filed on Mar. 15, 2004, now abandoned, each which is a continuation-in-part of application No. 10/027,611, filed on Oct. 24, 2001, now Pat. No. 6,702,894, and a continuation-in-part of application No. 10/028,450, filed on Oct. 24, 2001, now Pat. No. 6,962,715, and a continuation-in-part of application No. 10/625,813, filed on Jul. 22, 2003, now abandoned, and a division of application No. 09/877,896, filed on Jun. 7, 2001, now Pat. No. 6,623,785.

(51) Int. Cl.
*B05D 3/00* (2006.01)
*A61K 9/28* (2006.01)
*A61K 9/14* (2006.01)
*B29B 9/00* (2006.01)

(52) U.S. Cl. .................. 427/2.1; 427/2.14; 427/180; 264/5; 424/489

(58) Field of Classification Search ............... 427/2.14, 427/212–222; 424/489, 490
See application file for complete search history.

(56) References Cited

U.S. PATENT DOCUMENTS

| 4,517,173 | A  | * | 5/1985  | Kizawa et al. ............... 424/435 |
| 5,894,841 | A  | * | 4/1999  | Voges .................... 128/203.12 |
| 6,702,894 | B2 |   | 3/2004  | Lee et al. |
| 6,746,635 | B2 |   | 6/2004  | Mathiowitz et al. |
| RE38,629  | E  |   | 10/2004 | Bonhomme et al. |
| 6,808,934 | B2 |   | 10/2004 | Mutz et al. |
| 6,824,791 | B2 |   | 11/2004 | Mathiowitz et al. |

(Continued)

FOREIGN PATENT DOCUMENTS

WO    WO 0115664 A2  *  3/2001

OTHER PUBLICATIONS

"The Effect of Cosolvents on the Formulation of Nanoparticles From Low-Molecular-Weight Poly(I)lactide", Peltonen et al., AAPS PharmSciTech 2002; 3 (4) article 32 (www.aapspharmscitech.org).

*Primary Examiner*—Timothy H Meeks
*Assistant Examiner*—Cachet I Sellman

(57) ABSTRACT

Nanoparticles of a deposited bioactive agent can be obtained by selecting a solvent composition, selecting a deposition substrate, preparing a solution of the bioactive agent in the solvent composition, and applying the solution to a substrate as a plurality of droplets, such that evaporation of the applied solution produces nanoparticles of the bioactive agent.

24 Claims, 4 Drawing Sheets

U.S. PATENT DOCUMENTS 6,830,760 B2  12/2004  Cave et al.
6,852,760 B1  2/2005  Fine et al.
6,862,890 B2 *  3/2005  Williams et al. ............... 62/64
2004/0220081 A1  11/2004  Kreitz et al.

* cited by examiner

FIG. 1

```
                    ↙ 40
        ┌──────────────┐
        │    DATA      │
        │  INTERFACE   │
        │      30      │
        └──────────────┘
        ┌──────────┐   ┌──────────────┐
        │ CONTROL  │   │  DEPOSITING  │
        │SUBSYSTEM │───│SUBSYSTEM  36 │  42
        │    32    │   └──────────────┘
        │          │        ⇓ ⇓ ⇓      18
        │          │   ─────────────
        │          │   ┌──────────────────────┐
        │          │───│ POSITIONING SUBSYSTEM│
        │          │   │          34          │
        └──────────┘   └──────────────────────┘
        BIOACTIVE AGENT APPLICATION SYSTEM   10
```

SELECT A TARGET PARTICLE MORPHOLOGY
FOR A BIOACTIVE AGENT
102

PREPARE A SOLUTION OF THE BIOACTIVE
AGENT
104

APPLY THE SOLUTION TO A SUBSTRATE TO
FORM PARTICLES HAVING THE TARGET
MORPHOLOGY
106

```
SELECT A SOLVENT SYSTEM FOR
PREPARING A TARGET PARTICLE
MORPHOLOGY FOR A BIOACTIVE AGENT
                                    202
```

```
PREPARE A SOLUTION OF THE BIOACTIVE
AGENT IN THE SELECTED SOLVENT SYSTEM
                                    204
```

```
APPLY THE SOLUTION TO A SUBSTRATE TO
FORM PARTICLES HAVING THE TARGET
MORPHOLOGY
                                    206
```

```
PREPARE A SECOND SOLUTION OF
THE BIOACTIVE AGENT
                                    208
```

```
APPLY THE SECOND SOLUTION TO THE
PARTICLES
                                    210
```

PREPARATION OF NANOPARTICLES

CROSS REFERENCE TO RELATED APPLICATIONS

This application is a continuation-in-part of U.S. patent application Ser. Nos. 10/801,379, 10/801,380, and 10/801,381, each now abandoned and filed on Mar. 15, 2004, each of which is a continuation-in-part of U.S. patent application Ser. No. 10/027,611, now U.S. Pat. No. 6,702,894 and Ser. No. 10/028,450, now U.S. Pat. No. 6,962,715, both filed on Oct. 24, 2001, and Ser. No. 10/625,813, now abandoned, was filed on Jul. 22, 2003, and is a divisional of U.S. patent application Ser. No. 09/877,896, now U.S. Pat. No. 6,623,785, filed Jun. 7, 2001. The contents of the above identified applications and patent are incorporated by reference.

BACKGROUND

Oral administration of pharmaceuticals is one of the most widely used methods of providing therapy to treat a variety of illnesses. Many medications are orally administered to a person in a dosage form such as a tablet, capsule, or liquid. Such medications can be administered buccally, sublingually, or swallowed for release into the digestive tract.

In order for a drug to achieve its desired result, it typically must be delivered to a biological site of interest. The vast majority of drugs in use today are solid ingestibles. In order for these drugs to be absorbed into the bloodstream and transported to a biological site of interest, they usually must first be dissolved and then permeate the intestinal walls. The drugs must also avoid first pass metabolism, which occurs when the drugs are removed from the bloodstream as they pass through the liver.

Modern high throughput screening and combinatorial chemistry drug discovery methods may be used to produce high potency drugs with high specificities. As affinities for targeted cell sites increase, however, the lipophilicity of the compounds tends to increase. Conversely, the aqueous solubility of the compounds tends to decrease. A decrease in the aqueous solubility of a compound typically results in a corresponding decrease in the dissolution rate of the compound. A drug with a low dissolution rate may pass through the digestive system without being absorbed in therapeutic quantities. Therefore, methods of delivering bioactive agents with high dissolution rates are desired. Drug candidates are frequently chemically modified to enhance their specificity, permeability, solubility, and dissolution rate, and trade-offs between these desired factors are made as the drug candidates are refined.

The preparation of small particles may increase the solubility and potentially the bioavailability of a selected drug candidate. Solubility may be modified by physically grinding a drug to yield micron size and smaller particles. However, this mechanical particle size reduction can cause chemical and/or physical degradation of the drug by shear and heat stress. Furthermore, particles less than 5 microns tend to agglomerate, which counters the benefits of micronization. Although agglomeration can be limited by creating liquid suspensions or emulsions, such liquids can have poor storage life because they can suffer from accelerated thermal degradation relative to solid state formulations.

Spray-drying and freeze-drying also may be used to generate small particles in an attempt to increase drug dissolution rates, and therefore bioavailability. However, agglomeration remains a problem. Another approach relies on the dissolution of the drug in organic solvents and subsequent precipitation by the addition of water or some other miscible solvent in which the drug is less soluble. However, it may be difficult or impossible to produce small particles with this method. Yet another alternative is to increase the dissolution rate of the drug by complexing the active drug entity with inclusion agents like cyclodextrins. For this to work the drug molecule should be amenable to inclusion into the cyclodextrin ring. Even then, the drug-cyclodextrin complex should be extensively tested for safety, which can be time consuming and expensive. Another approach utilizes the precipitation of a drug-polymer mixture, resulting in the production of small (i.e. micrometer-sized) particles are produced. However, in this case, the polymer typically remains as an "additive" in the resulting particles.

BRIEF DESCRIPTION OF DRAWINGS

FIG. 1 schematically shows an exemplary system configured to apply a bioactive agent to a delivery substrate according to an embodiment of the invention.

FIG. 2 schematically shows an exemplary dosage form including a delivery substrate and an applied bioactive agent, according to an embodiment of the invention.

FIG. 3 schematically shows an exemplary sheet including plural dosage forms, according to an embodiment of the invention.

FIG. 8 schematically shows exemplary dots of bioactive agent having different dot patterns, according to an embodiment of the invention.

FIG. 9 is a flowchart showing a method of preparing a desired morphology of a bioactive agent, according to an embodiment of the invention.

FIG. 10 is a flowchart showing an alternative method of preparing a desired morphology of a bioactive agent, according to an embodiment of the invention.

DETAILED DESCRIPTION

Figure 4:
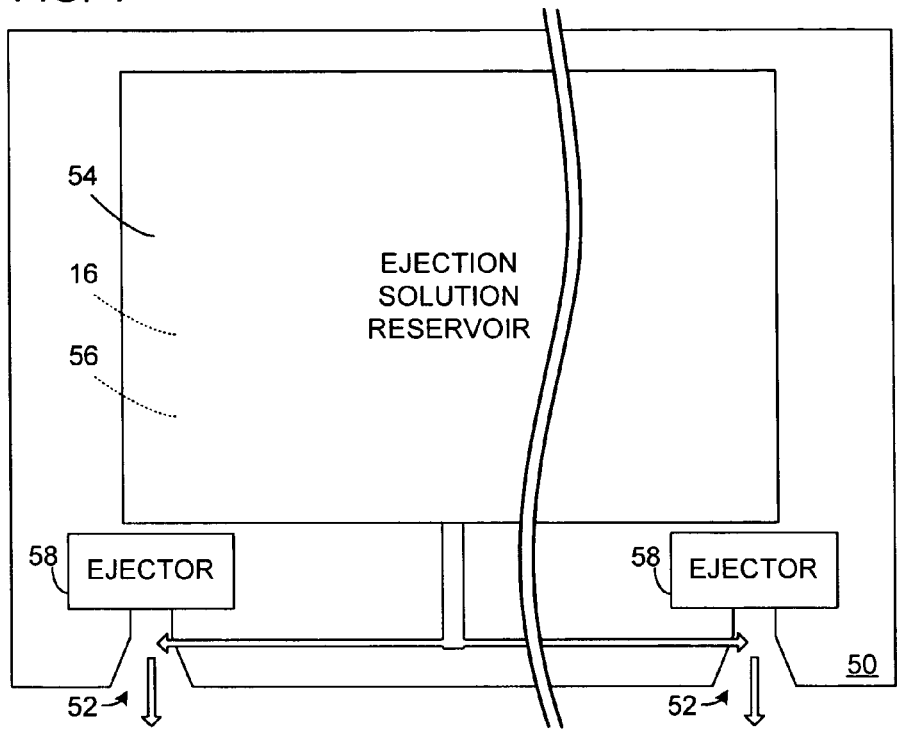
FIG. 4 schematically shows a portion of an exemplary depositing subsystem configured to eject a solution including a bioactive agent onto a delivery substrate, according to an embodiment of the invention.

FIG. 1 schematically shows a system 10 adapted to apply a bioactive agent to a delivery substrate. For purposes of this description, the term "bioactive agent" is used to describe a composition that affects a biological function of an animal, such as a human. A nonlimiting example of a bioactive agent is a pharmaceutical substance, such as a drug, which is given to alter a physiological condition of the animal. A bioactive agent may be any type of drug, medication, medicament, vitamin, nutritional supplement, or other composition that can affect the animal.

As mentioned above, system 10 is adapted to apply a bioactive agent to a delivery substrate. As used herein, a "delivery substrate" is used to describe a medium onto which one or more bioactive agents may be applied. The delivery substrate can be coated with receiving layers such as polyvinyl alcohol, hydrogels, polytetrafluoroethylene, or other tailored biocompatible films. A delivery substrate, one or more applied bioactive agents, and other applied substances can be collectively referred to as a dosage form, which may be configured to be taken by an animal recipient. FIG. 2 schematically shows such a dosage form 12, which includes a delivery substrate 14, and an applied bioactive agent 16. It should be understood that the dosage form may also include one or more auxiliary components. Alternatively, the delivery substrate may be selected for the preparation of a selected morphology of the bioactive agent that, once prepared, may be collected from the delivery substrate and administered to an animal recipient via another dosage form. For example, the applied bioactive agent may be collected, then administered via inhalation of an aerosol, or via a soluble capsule, among others.

As shown in FIG. 3, a delivery substrate may be configured as a sheet 18 that includes a plurality of discrete dosage portions 20 onto which a desired amount of bioactive agent can be applied to produce a dosage form. The bioactive agent can be applied to each of the plurality of dosage portions and then the dosage portions may be separated from one another for individual delivery to one or more recipients. Sheet 18 is provided as a nonlimiting example, and doses may be applied to delivery substrates taking different forms. For example, a roll of substrate may be used for high speed production of dosage forms. It is within the scope of this disclosure to individually apply only a single dose of a bioactive agent to a delivery substrate at a particular time, or to instead apply plural doses to a corresponding plurality of different dosage portions. In other words, dosage forms may be prepared one at a time or several at the same time, or at least one after the other, without limitation.

A dosage form can be configured for oral delivery, topical delivery, or any other suitable delivery mode. When configured for oral delivery, a dosage form may be configured to be ingested or the dosage form may be configured to be removed from the oral cavity after the bioactive agent is released. When configured for ingestion, the delivery substrate can be configured to dissolve or degrade in body fluids and/or enzymes, or the delivery substrate can be made of non-degradable materials that are readily eliminated by the body. The delivery substrate may be hydrophilic and readily disintegrate in water. Alternatively, the delivery substrate may be substantially hydrophobic, such that the substrate does not readily degrade upon ingestion. Additionally, or in the alternative, the delivery substrate may include a combination of hydrophilic and hydrophobic properties. Furthermore, the delivery substrate may be configured so that dissolution or disintegration is enabled, or enhanced, at the pH of the fluids in the stomach or upper intestine.

Materials used to construct a delivery substrate may be selected to improve the final dosage form. For example, the substrate properties can be tailored to receive the impinging drops in an optimized fashion and to release corresponding solvents as required. The delivery substrate may be configured to minimize unintended interactions with the bioactive agent dispensed on the delivery substrate. The delivery substrate may also be configured to remain stable over extended periods of time, at elevated temperatures, and at high or low levels of relative humidity. In addition, a delivery substrate can be configured to resist the growth of microorganisms. Further, a delivery substrate may be configured with reasonable mechanical properties, such as tensile strength and tear strength.

A delivery substrate may include polymeric and/or paper organic film formers. Nonlimiting examples of such substrates include starch (natural and chemically modified), glycerin based sheets with or without a releasable backing, and the like; proteins such as gelatin, wheat gluten, and the like; cellulose derivatives such as hydroxypropylmethylcellulose, methocel, and the like; other polysaccharides such as pectin, xanthan gum, guar gum, algin, chitosan, pullulan (an extracellular water-soluble microbial polysaccharide produced by different strains of *Aureobasidium pullulans*), and the like; sorbitol; seaweed; synthetic polymers such as polyvinyl alcohol, polymethylvinylether (PVME), poly-(2-ethyl 2-oxazoline), polyvinylpyrrolidone, and the like. Further examples of edible delivery substrates are those that are based on milk proteins, rice paper, potato wafer sheets, and films made from restructured fruits and vegetables. It should be understood that one or more of the above listed substrate materials, as well as other substrate materials, may be used in combination in some embodiments.

Using an ingestible delivery substrate containing a water-expandable foam can facilitate the rapid release of the bioactive agent once taken by the recipient. Examples of such materials are an oxidized regenerated cellulose commercially available from Johnson and Johnson under the trademark SURGICEL®, and a porcine derived gelatin powder commercially available from Pharmacia Corporation under the trademark GELFOAM®.

Alternatively, a delivery substrate may exhibit surface characteristics selected to enhance the preparation of a selected particle morphology of the deposited bioactive agent. Additionally, or in the alternative, the delivery substrate may be selected to facilitate the deposition and preparation of a selected particle morphology, wherein the resulting particles are collected from the substrate. In this aspect of particle preparation, the delivery substrate is not necessarily suited for ingestion.

As schematically shown in FIG. 1, system 10 includes a data interface 30, a control subsystem 32, a positioning subsystem 34, and a depositing subsystem 36. Systems similar to system 10 have been used for printing extremely small droplets of ink onto paper to create an image. Such systems are commonly referred to as "inkjet" printing systems. Although system 10 is depicted as utilizing a thermal inkjet printing apparatus, it should be appreciated that the bioactive agent may be applied to the substrate by any of a variety of other delivery systems, including but not limited to piezoelectric ejection, aerosol generation, micropipettes, pipettes, and any other delivery system that can be configured to dispense a selected volume of solution with the desired application parameters.

As described herein, for example, the technology used to print ink onto paper may be adapted to apply a bioactive agent to a delivery substrate. Such application systems are highly refined and can be used in high volume industrial applications and/or low volume personal applications. Highly developed printing methods can be adapted to fabricate and control drug production in a very reproducible and high speed process. Furthermore, it should be understood that advances in inkjet printing technology may be utilized to precisely apply a bioactive agent to a delivery substrate, thereby enhancing control of the dissolution rate of the bioactive agent.

Control subsystem 32 can include componentry, such as a printed circuit board, processor, memory, application specific integrated circuit, etc., which effectuates application of a bioactive agent onto the delivery substrate in accordance with received information 40. Information 40 may be received via a wired or wireless data interface 30, or other suitable mechanism. Such information may include instructions for applying a particular bioactive agent to the delivery substrate according to one or more application parameters. Upon receiving such instructions, the control subsystem can cause positioning subsystem 34 and depositing subsystem 36 to cooperate to apply a bioactive agent to a sheet 18 of delivery substrate 14, thus producing a dosage form 12 that may be taken by a recipient.

Positioning subsystem 34 can control the relative positioning of the depositing subsystem and the delivery substrate onto which the bioactive agent is applied. For example, positioning subsystem 34 can include a sheet feed that advances the delivery substrate through an application zone 42 of the depositing subsystem. The positioning subsystem can additionally or alternatively include a mechanism for laterally positioning the depositing subsystem, or a portion thereof, relative to the delivery substrate. The relative position of the delivery substrate and the depositing subsystem can be controlled so that the bioactive agent is applied onto only a desired portion of the delivery substrate.

FIG. 4 schematically shows a portion of an exemplary depositing subsystem in the form of an ejection cartridge 50, which may include one or more nozzles 52 adapted to eject bioactive agent 16 onto a delivery substrate. The bioactive agent can be ejected as a constituent element of an ejection solution 54 that includes a carrier solvent 56, such as ethanol. The bioactive agent can be ejected onto the delivery substrate in the form of an ejection "drop." The size, geometry, and other aspects of nozzle 52 can be designed to reliably eject drops having a desired volume. Current application systems can apply drops ranging from as small as nanoliters to femtoliters, and even smaller drop sizes may be possible. Each nozzle can be similarly configured so that ejected drops have approximately the same volume.

As shown in FIG. 4, a nozzle can be associated with an ejector 58, such as a resistor, that is operatively connected to a control subsystem. Ejector 58 is designed to cause drops of ejection solution 54 to be ejected through a nozzle 52. In embodiments that utilize a resistor as an ejector, the control subsystem may activate the resistor by directing current through the resistor in one or more pulses. Each ejector can be configured to receive an ejection pulse via a conductive path that leads to the ejector. The control subsystem can route current to the individual ejectors through such conductive paths based on received instructions. Ejection pulses can be used to selectively cause the ejector to heat the ejection solution and at least partially vaporize the solution to create an ejection bubble. Expansion of the ejection bubble can cause some of the solution to be ejected out of the corresponding nozzle onto the delivery substrate. It is appreciated that droplets generated using piezoelectric ejectors may also be used to apply bioactive agent to the delivery substrate. In either case, ejection of the solution can be precisely timed to fire onto a desired portion of the delivery substrate, the relative position of which may be controlled by the positioning subsystem with great accuracy. The control subsystem can cause the various ejectors to eject the bioactive agent through the corresponding nozzles onto the desired portions of the delivery substrate in accordance with received instructions, such as instructions received in the form of an application signal.

Application of bioactive agent onto a delivery substrate in the form of ejected drops produces a "dot" of the bioactive agent on the delivery substrate. The term "dot" is used to refer to the bioactive agent drop once it contacts the delivery substrate. In some examples, the bioactive agent in the drop will stay in a thin layer near the surface of the substrate. However, some substrates can be porous, and when the drop contacts the substrate the bioactive agent can spread outward and/or penetrate into the substrate resulting in dot gain and/or penetration. Dot gain is the ratio of the final diameter of a dot on the substrate to its initial diameter. Dot penetration is the depth that the drop soaks into the substrate. The physical and/or chemical properties of the dots can enhance dissolution rates without disrupting the permeability and specificity of the bioactive agent. Controlled dot placement, high surface-to-mass ratio of the dots, and digital mass deposition control of the dots can be used to address significant dissolution rate and dosage control issues faced by the pharmaceutical industry.

Figure 5:
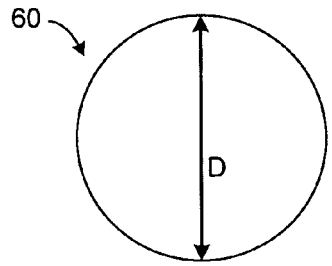
FIGS. 5 and 6 show an exemplary drop of solution applied to an exemplary delivery substrate, according to an embodiment of the invention.
Figure 6:
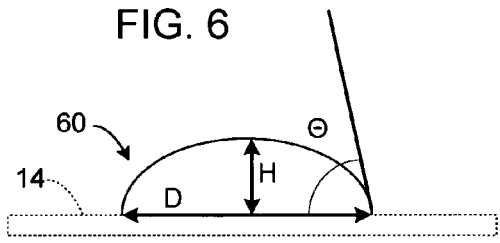

FIGS. 5 and 6 schematically show an exemplary dot 60 on a delivery substrate 14. Dot 60 has virtually no dot gain or dot penetration, as may be the case when an ejection solution is applied to a delivery substrate having a polytetrafluoroethylene, paraffin, or other nonwettable, surface, or a relatively impermeant surface, such as a metal or glass substrate Application to such surfaces may be used in the preparation of selected particle morphologies, and is also used herein for the purpose of simplicity. It should be understood that the general principals set forth in this disclosure also can apply when ejection solution is applied to a wettable delivery substrate.

Exemplary dot 60 is half of an oblate spheroid, characterized by a substantially circular horizontal cross-section having a diameter D (where radius R=D/2) and a substantially elliptical vertical cross section having a height H. The geometric surface area (S) of dot 60 is given by the following equation:

$$S = \frac{1}{2}\left(2\pi R^2 + \pi \frac{H^2}{e} \ln\left(\frac{1+e}{1-e}\right)\right)$$

As described in more detail below, the geometric surface area of a dot can affect attributes of the bioactive agent, such as dissolution rate of the bioactive agent. It should be understood that dot 60 is provided as a nonlimiting example, and other dot geometries are possible. The geometric surface area of such differently shaped dots can also affect attributes of the bioactive agent, such as dissolution rate of the bioactive agent.

One convenient way of quantifying the nature of the interaction between the solution forming the dot and the surface of the delivery substrate, is to measure the angle θ formed by the liquid-solid and the liquid-air interfaces. This angle, referred to as the contact angle, is a product of the surface tension of the solution as well as the wettability of the delivery substrate. Solvents having a high surface tension, and poor interaction with the surface of the delivery substrate tend to exhibit contact angles greater than 90°. The solution then tends to form discrete droplets on the surface. However, where the solvent is relatively nonpolar, as is typically the case with an organic solvent, and the delivery substrate is similarly nonpolar, such as in the case of a waxy surface, the contact angle is typically less than 90°, and the liquid tends to spread out and form a thin film. As the dot spreads out and thins, the contact angle tends to zero.

A depositing subsystem may be adapted to apply one or more different bioactive agents, which may be carried in corresponding ejection solutions. In some embodiments, a depositing subsystem may include two or more ejection cartridges that are each configured to apply a different bioactive agent to a corresponding delivery substrate and/or eject solution having different drop volumes. Furthermore, a depositing subsystem may be configured to interchangeably receive different ejection cartridges, which are individually configured to apply different bioactive agents to corresponding delivery substrates. Interchangeable ejection cartridges may also be used to replace an empty ejection cartridge with a full ejection cartridge. It is within the scope of this disclosure to utilize other mechanisms for applying a bioactive agent onto a delivery substrate, and ejection cartridge 50 is provided as a nonlimiting example. For example, a depositing subsystem may include an ejection cartridge that utilizes an ejection-head having ejectors configured to effectuate fluid ejection via a nonthermal mechanism, such as vibrational displacement caused by a piezoelectric ejection element.

As described herein, application systems, such as system 10, can be used to prepare a dosage form that includes a bioactive agent with a selected target morphology. Application systems can very accurately place small drops of ejection solution onto a delivery substrate. Ejection of bioactive agents through application devices has been demonstrated as non destructive to small and large molecule bioactive agents. The method involves no chemical modification of the bioactive agent which might affect the effectiveness of the bioactive agent or cause undesired side effects. It is similar to dissolution and reprecipitation of a drug onto a suitable substrate.

Digitally addressable application technology enables highly reproducible deposition of bioactive agents for morphology control. Application systems can actively measure drop sizes and nozzle malfunctions, and use such information to accurately dispense bioactive agent by correcting and/or compensating for any irregularities. Furthermore, the bioactive agent may be applied to a delivery substrate in virtually unlimited different dot patterns, dot sizes, dot shapes, etc.

The deposition characteristics of a bioactive agent on a delivery substrate can be influenced by the manner in which the bioactive agent is applied to the delivery substrate. As used herein, "deposition characteristic" is used to refer to a physical and/or chemical characteristic of a bioactive agent, as applied to a delivery substrate. The deposition characteristics can affect attributes of the bioactive agent, such as bioavailability, and dissolution rate, among others. Nonlimiting examples of deposition characteristics include dot size, dot geometric surface area, dot mass, dot surface-to-mass ratio, dot topography, dot topographic surface area, dot geometry, dot layering, morphology, solubility, and physico- and/or chemico-interactions between the bioactive agent and the delivery substrate (e.g. covalent, ionic, hydrogen bonding). Such deposition characteristics can heavily influence the attributes of a dosage form. For example, dissolution rate is directly proportional to surface area, as demonstrated by the Noyes-Whitney Equation:

$$dc/dt = k*S*(C_s - C_b)$$

Where: $dc/dt$ = dissolution rate
$k$ = dissolution rate constant
$S$ = surface area
$C_s$ = saturation concentration
$C_b$ = bulk solution concentration Therefore, the ability to control deposition characteristics can provide a high level of control over the attributes of the dosage form, such as the dissolution rate of the bioactive agent on the dosage form.

A bioactive agent can be applied to a delivery substrate in a highly controlled manner. In particular, a depositing subsystem can be configured so as to eject drops having a desired size. As mentioned above, drop size can be very small, and small drop size can facilitate small dot size. Furthermore, a positioning subsystem can cooperate with a depositing subsystem to precisely place drops on a substrate. A depositing subsystem can be configured to generate a desired drop size for a particular bioactive agent. The drop size and drop pattern, as well as other characteristics of the applied bioactive agent, are highly repeatable. Therefore, dosage forms can be produced with a high degree of consistency.

Application parameters, which correspond to the manner in which the bioactive agent is applied to the delivery substrate and/or the configuration of the application system, can be set so that the bioactive agent will have desired deposition characteristics on the delivery substrate. Application parameters can be set based on a target dissolution rate, which can be achieved when the bioactive agent is applied to a delivery substrate according to the set application parameters. Non-limiting examples of application parameters which may be set to affect deposition characteristics, and consequently dissolution rates, include nozzle size, nozzle shape, chamber size, chamber shape, pulse character, firing frequency, firing modulation, burst number (number of drops fired at a particular frequency over a particular period of time), firing energy, turn-on-energy, pulse warming, back pressure (pressure at which fluid is supplied to chamber and/or nozzle), substrate temperature, drop spacing, deposition patterns, number of passes, drying methods (ambient temperature, solution temperature, solvent vapor pressure, etc.), dry time between passes, bioactive agent concentration in the ejection solution, solution viscosity, solution surface tension, and solution density.

Application parameters can be organized into primary and secondary application parameters. Primary application parameters can be selected to determine a broad range of the drop size or composition utilized to form the dots on the delivery substrate. Non-limiting examples of primary application parameters include nozzle geometry (nozzle dimensions and shape), resistor size, firing chamber geometry, drying methods, and bioactive fluid properties. Some primary application parameters are substantially fixed, meaning that they are set before application of the bioactive agent is initiated. Primary application parameters can be specified to generally determine the coarse or approximate values for drop size and composition.

Secondary application parameters can be selected to determine a narrower range for drop size within the broader range discussed above. Non-limiting examples of secondary application parameters include fire pulse parameters (pulse shape, voltage, current, or duration), pulse warming parameters, firing frequency, back pressure, burst number, and ejector substrate temperature. Some secondary application parameters are variable, meaning that they can be selectively modified after the application system is created to modulate a drop size or other characteristics to within a tolerance.

One or more primary and/or secondary application parameters can be set to achieve a desired dot size, which can affect a deposition characteristic, including the surface-to-mass ratio of the bioactive agent on the delivery substrate. For example, the dot size of the applied bioactive agent can be kept relatively small by applying relatively small drops to a delivery substrate. Current application systems can apply drops ranging from nanoliters to femtoliters, and even smaller drop sizes may be possible. Nozzle size and chamber size are exemplary application parameters that can be set to achieve small drop sizes. The application of very small drops to a suitable delivery substrate can facilitate very high geometric surface-to-mass ratio application of the bioactive agent in a very repeatable and predictable process. The variability in drop volumes ejected from an ejection cartridge, such as a thermal ejection cartridge or a piezoelectric ejection cartridge, can be substantially less than the variability previously achievable using prior art application methods. Using current ejection cartridge manufacturing procedures, the standard deviation in drop volume may be approximately 10% to approximately 25% or less of the mean drop volume, and even smaller standard deviations are possible. In contrast, other methods of applying a pharmaceutical to a delivery substrate, such as aerosol spraying, may have a standard deviation of approximately 40% or greater of the mean drop volume. In particular, such methods have not been able to consistently produce a standard deviation of 15% or less, which is achievable using the systems and methods described herein. In other words, ejection of a solution through a precisely manufactured nozzle, as described herein, can be substantially more consistent and controllable than other application methods. Furthermore, consistent drop volume can facilitate consistent dot size, such as where a standard deviation for a geometric surface-to-mass ratio of the dots is less than approximately 15% of a mean geometric surface-to-mass ratio of the dots.

Dot characteristics may also be modified by altering the concentration of dissolved bioactive agent in an ejection solution and/or by modifying solvent removal rates, which can be influenced by application parameters such as solvent composition (low flash point), drop size, drying temperature, and/or vapor pressure. For example, smaller drops tend to increase the removal rate of solvent due to more proportional droplet surface area, and increased temperatures (e.g. solution, ambient, and/or substrate) tend to enhance evaporation of the solvent. In some embodiments, depositing system 36 can include a heating assembly, such as an IR/convection oven, to heat up and evaporate unwanted solvents from the delivery substrate after the bioactive agent has been deposited. The ability to apply a bioactive agent with a small dot size facilitates high dissolution rates because the same amount of bioactive agent may be applied in many small dots, which have a relatively high net geometric surface area, instead of in fewer large dots, which have a relatively small net geometric surface area.

Figure 7:
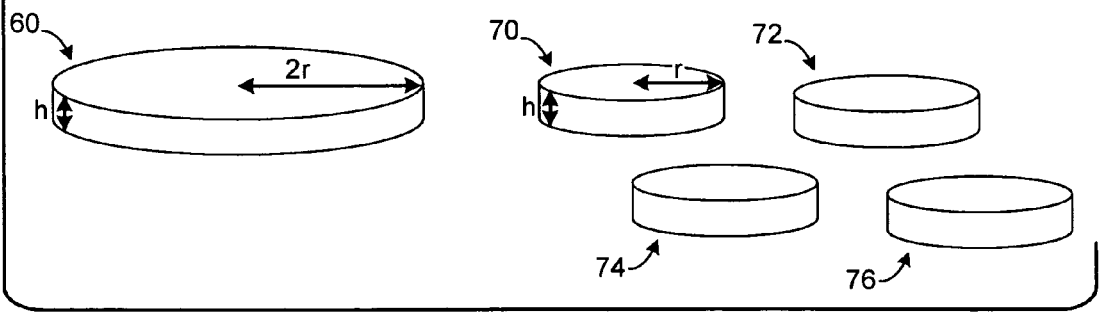
FIG. 7 schematically shows exemplary dots of bioactive agent having different geometric surface areas, according to an embodiment of the invention.

FIG. 7 schematically shows how small dot size can increase surface-to-mass ratio, and therefore increase dissolution rate. As illustrated, dot 60 has an exemplary cylindrical volume equal to $V=4\pi r^2 h$, and dots 70, 72, 74, and 76 each have exemplary cylindrical volumes equal to $V=\pi r^2 h$. Therefore, the four smaller dots have the same collective volume as the larger dot. Assuming equal densities, the smaller dots also collectively have the same mass as the larger dot. However, the larger dot has a geometric surface area equal to $S=4\pi r(h+r)$, while the geometric surface area of one of the smaller dots is equal to $S=\pi r(2h+r)$. Therefore, the net geometric surface area of the four smaller dots combined is equal to $S=4\pi r(2h+r)$. As can be seen, assuming cylindrical geometry, the surface area of the 4 smaller dots will be larger than the surface area of the larger dot if the heights of the dots do not equal zero. The above example shows dots that have cylindrical geometries for the purpose of simplicity. However, it should be understood that substantially more complicated drop geometries are possible, and small relative dot size can improve the net geometric surface-to-mass ratio for such geometries.

The deposition pattern of drops applied to the delivery substrate is another nonlimiting example of an application parameter that may be used to affect a deposition characteristic, including the surface-to-mass ratio, of the bioactive agent on the delivery substrate. In particular, the surface-to-mass ratio can be controlled by selecting the spacing between adjacent drops. Sufficient spacing between adjacent drops can prevent adjacent dots from coalescing, which tends to decrease the geometric surface-to-mass ratio. Conversely, drops may be applied sufficiently close to one another to effectively build up the bioactive agent so as to have a lower geometric surface-to-mass ratio than would be present in separated dots having the same net mass. The same amount of a bioactive agent may be applied with different dot spacing, which can correspond to different surface-to-mass ratios, thereby permitting customized deposition characteristics for the bioactive agent. Application systems can precisely place drops, such as consistently within at least approximately $1\times10^{-5}$ meters (10 microns) of an intended target on the delivery substrate. Such precise placement facilitates highly reproducible dot patterns.

Drop placement, or more precisely, drop precision of approximately $1\times10^{-5}$ meters is sufficient for an application system to precisely place about 2400 discrete drops per inch. A 2400 drops per inch application system can produce a dot to dot spacing of approximately 11 microns. More precise drop placement is possible by setting one or more parameters to achieve improved placement accuracy. For example, a nozzle can be designed with a long bore to achieve greater precision. Sustained precision can be maintained by frequently cleaning nozzles of the depositing subsystem, thereby reducing stray solution droplets that may puddle and dry around the nozzle and thereby affect ejection accuracy. Precise drop placement may also be influenced by controlling drop firing velocity (speed and direction).

Decreasing nozzle-to-substrate distance can reduce the effect of drop speed variability on drop precision by minimizing the area in which drops may land. Drops can decelerate between the nozzle and the substrate due to factors such as air resistance. Smaller drop volumes can correspond to faster deceleration rates due to less drop momentum. When a drop is fired at a speed higher than average, it can land on the substrate slightly before a targeted location. Conversely, when a drop is fired at a slower than average speed, it can land after a targeted location. Furthermore, variability introduced in drop trajectory and/or the relative speed between the substrate and the nozzles can be exaggerated over longer drop firing distances. Therefore, decreasing nozzle-to-substrate distance can help reduce some variability that could limit drop precision. However, some types of substrate may swell, and nozzles can be spaced sufficiently to avoid contacting the substrate. A nozzle-to-substrate distance of approximately 0.5 to 1.3 millimeters has been found to provide adequate spacing while limiting drop placement variability to an acceptable level. Control of the above described exemplary parameters enables drops to be very precisely placed compared to other known application methods.

Alternatively, the nozzle-to-substrate distance can be increased or otherwise varied in order to facilitate solvent evaporation from the ejected drop while the drop is in flight to the substrate. The resulting degree of evaporation may be selected to simply increase the concentration of the bioactive agent in the deposited droplet, increase the rate of particle nucleation in the deposited droplets, or even deposit substantially dry (i.e. solvent-free) bioactive agent due to evaporation during the droplet's flight to the substrate.

Drops can be placed so that they are spaced apart from each other or drops can be purposefully placed at least partially on top of one another. In either case, each ejected drop can be precisely placed in a desired location. Drop placement does not have to be left to random chance, as may be the case using other application methods, such as aerosol spray delivery. Precise drop placement can be used to effectuate a desired dot pattern or dot spacing. The relative spacing of two or more adjacent drops can change the surface-to-mass ratio of applied dots, and therefore control the dissolution rate of the applied bioactive agent.

For example, FIG. 8 schematically shows four alternate dot patterns corresponding to four different surface-to-mass ratios. Dots 80*a* and 80*b* are spaced apart from one another, and do not overlap. Dots 82*a* and 82*b* are spaced closer together, and slightly overlap. Dots 84*a* and 84*b* are spaced even closer together, and there is considerable overlap between the two dots. Finally, dots 86*a* and 86*b* are spaced one on top of the other, completely overlapping. In general, surface-to-mass ratio will decrease as the amount of dot overlap increases. Therefore, dots 80*a* and 80*b* have the highest collective surface-to-mass ratio, while dots 86*a* and 86*b* have the lowest collective surface to mass ratio. As described above, dissolution rate relates to the surface-to-mass ratio. Therefore, dot spacing can be selected to achieve a desired dissolution rate.

Although described in the context of two dots, it should be understood that spacing between three or more dots may be selected to further achieve a desired dissolution rate. The spacing between all applied dots may be substantially the same for all dots, or the dots may be arranged in a pattern in which the spacing varies, such as in a repeating pattern. In either case, a high level of control over drop placement enables drops to be applied so that a standard deviation of distance between adjacent dots is less than approximately 15% of a mean distance between adjacent dots. As used in this context, adjacent dots means pairs of dots that are intended to have the same spacing as other pairs of dots. Dots that are purposefully spaced at a different distance are not considered adjacent in this context. As mentioned above, some dots can be purposefully overlapped. A high level of control over drop placement enables drops to be applied so that a standard deviation of combined geometric surface area of overlapping dots is less than approximately 15% of a mean combined geometric surface area of overlapping dots.

Dots having different sizes (corresponding to drops with different sizes, for example), may be precisely positioned to achieve a desired dissolution rate. It should be understood that FIG. 8 schematically represents dots as cylinders, and that actual dot geometry can be considerably more complex. Nonetheless, the ability to precisely control drop placement, and therefore dot pattern, can be used to control the relative dissolution rate for virtually any dot geometry.

Dot shape and/or topography are also deposition characteristics which can be influenced by application parameters. As used herein, dot shape refers to the general shape of a dot without reference to surface detail, and dot topography is used to refer to surface detail of the dot. Dot shape and/or topography can have a great effect on the topographic surface area of a dot. A highly textured surface can provide much more surface area than a smooth surface. The amount of topographic surface area typically directly corresponds to the probability that the dot will dissolve. In other words, a dot exposed on many sides, and therefore having less three-dimensional crystal lattice stabilization and a greater surface area, is more likely to readily dissolve than a dot with less exposure and more stabilization. Application parameters that can be set to affect topographical surface area based on shape and/or topography include bioactive agent concentration in the ejection solution, and those parameters affecting drop size and solvent removal rates.

One or more primary and/or secondary application parameters can also be set to achieve a desired particle morphology. Particle morphology is yet another nonlimiting example of a deposition characteristic which can influence the attributes of a dosage form. As used herein, morphology may refer to particle size, particle shape, crystalline form, polymorphic form, or any combination thereof. Some bioactive agents may have multiple polymorphic forms, including amorphous (substantially noncrystalline) forms. Depending upon the bioactive agent, the solvent, the nature of the substrate, and particular application parameters selected, application of the bioactive agent to the substrate may result in generation of the desired morphology.

Upon evaporation of solvent, the bioactive agent may form any of a variety of morphologies, including discrete particles. Such particles may be formed of material having a single crystalline phase, or a single-phase material. Alternatively, the particles may include multiple distinct crystalline phases, or be multi-phase materials. Where the particles are multi-phase materials, the particles may offer the appearance of being a single continuous phase, by virtue of being multi-phasic with respect to individual particles, or by virtue of being phase-separated. The resulting bulk material may offer a uniform appearance. The particles may resemble needles, plates, rods, clusters, cubes, spheres, or other particle shapes. These particle shapes may or may not reflect the underlying crystalline structure of the particle. Where the particle has substantially no crystalline structure, the particle is amorphous.

Different crystal morphologies can be achieved by adjusting one or more of the following: the solvent system, the characteristics of the delivery substrate, and the application system used. Alternatively, or in addition, application parameters such as solvent formulation, drop size, removal rates, and crystal templates may be selected and/or adjusted. Crystal formation kinetics can drive a crystal form to different structures or mixtures of structures. Application parameters may be selected to favor the creation of a desired, or target morphology, in order to optimize one or more characteristics of the dosage form. In particular, the bioavailability of the bioactive agent may be affected by modification of one or more application parameters.

Desired morphologies may be reliably produced and stabilized where the application system can place precisely controlled solution formulations as consistently sized drops in a desired pattern, while having a high level of control over how the solution dries and/or other application parameters that may affect morphology.

In particular, the application parameters may be selected so that the resulting morphology of the bioactive agent includes particles having a desired size distribution. More specifically, it may be advantageous to prepare bioactive agent in the form of nanoparticles. Nanoparticles typically exhibit an average particle size of less than about 1 μm (1 micrometer, or micron). That is, the average size of the particles may be measured in nanometers. Such particles may offer advantages in bioavailability when administered to a patient.

By manipulating the solvent system used, the nature of the delivery substrate, the application system, and/or the application parameters selected, a target morphology may be obtained that results in a desired activity and/or bioavailability for the bioactive agent.

Bioactive agent application, as disclosed herein, may drive and control kinetic versus equilibrium phenomena more reproducibly and/or consistently than bulk processes. The kinetics and/or solvent removal may be tightly controlled by selection of an appropriate application system and/or appropriate application parameters, such as drop size, drop pattern, solution formulation, vapor pressure, temperature, etc. Because individual drops of solution containing the bioactive agent can be discretely applied to a delivery substrate, there is less risk of an undesired crystal form driving crystallization of an entire batch to an undesired structure (i.e. experiencing a seeding event). Furthermore, application of small drops onto a delivery substrate can minimize equilibrium effects because the kinetics associated with such application methods are very fast.

Because the ejected drops are quite small, the modification of application parameters can be used to affect processes occurring in the drop even before the drop reaches the substrate after ejection. Manipulation of ejected drop size, ejected drop velocity, ejected drop temperature, or a combination thereof may be used to effect the formation of a desired particle morphology, for example by modifying the rate of evaporation of solvent from the ejected drop. The formation of a target particle morphology is also dependent upon the solvent system used, as well as the physical characteristics of the bioactive agent applied.

As discussed above, ejected drop size may be broadly selected by application system used and/or modification of nozzle geometry, resistor size, and firing chamber geometry. Additional parameters that can be modified to achieve a selected drop size include pulse shape, pulse voltage, pulse current, pulse duration, pulse warming parameters, firing frequency, back pressure, burst number, and ejector substrate temperature. More particularly, ejected drop volume can be selected via modification of the pulse voltage, pulse width, and/or firing frequency at the ejector.

In particular, by dispensing a solution of an organic solvent using thermal ejection, very small ejected droplets may be generated. These low drop volumes (and diameters) result from the small nozzle and the low density, surface tension, and viscosities of the solutions used. For example, the viscosity and surface tension of ethanol are 30-50% that of water, and thus can yield stable droplets of smaller size compared to water-based solutions.

In addition, the ejector to delivery substrate distance may be varied so that a greater or lesser degree of solvent evaporation may occur while an ejected drop is in flight to the delivery substrate. The ejector to substrate distances may vary, for example, from about 1 mm to about 10 mm.

In particular, it has been found that by selection of appropriate application parameters, application of a bioactive agent to the delivery substrate may result in the formation of substantially amorphous microparticles. That is, the particles of bioactive agent remaining after evaporation of the deposited solution are substantially amorphous, in that they fail to exhibit a defined and substantially crystalline structure. Additionally, or in the alternative, the discrete particles of bioactive agent may exhibit a substantially narrow range of particle sizes, such as on the order of micrometers or nanometers. In one aspect, the application parameters are selected so that application of the bioactive agent to the delivery substrate results in the formation of nanometer-sized particles that are substantially amorphous, and substantially spherical in shape.

An amorphous material may be higher in free energy (compared to material that is substantially crystalline) and thus may be more soluble in aqueous media, potentially increasing bioavailability. However, although an amorphous form of a bioactive agent may be the fastest dissolving, it may also be the most unstable and difficult to consistently reproduce, store, and deliver. For example, amorphous materials may be less stable than substantially crystalline forms of the same materials. Amorphous particles may also provide for better powder control capabilities, and may permit more precise and accurate dosing, when compared to the preparation of conventional medicament tablets.

Suitable amorphous forms of a given bioactive agent can typically be formed by the addition of one or more additives to the solution to be deposited, such that drying of the deposited solution results in inhibition of the rate of phase separation and/or crystallization, therefore providing a kinetically stable formulation of the bioactive agent. Some hydrates and solvates can be more or less stable than the pure crystal forms and water can be absorbed or desorbed during storage.

The additional solution component may be an excipient, that is, an inert additive or carrier. Alternatively, the additive may have some specific or non-specific biological activity. The additional solution component may be a surfactant, an oil, or a polymer. Where the additive is a polymer, the polymer is typically biocompatible and substantially non-toxic.

The polymer additive may be a copolymer of polyoxyethylene and polyoxypropylene, such as those sold under the tradename LUTROL. In particular, the polymer additive may be LUTROL F127. Alternatively, the polymer additive may be a polymer or copolymer of polyvinylpyrrolidone (PVP). In yet another alternative, the polymer additive may be a derivative of hydroxypropyl methylcellulose, or HPMC. Additional suitable polymer additives include pullalan and cyclodextrins, among others. In particular, where the additive is a hydrophilic substance, such as a hydrophilic polymer, interaction between the bioactive agent and the hydrophilic substance may result in improved wetting of the resulting particles. Additionally, or in the alternative, the polymer additive may be selected to facilitate collection of deposited material from a substrate, particularly where the substrate is an impermeant substrate that is not necessarily suited for ingestion. In this aspect, the presence of the polymer additive may provide additional strength and cohesion to the resulting particles, facilitating their collection.

Typically, the solution is formulated such that in the resulting nanoparticles the bioactive agent and the additive are dispersed throughout the resulting nanoparticle volume, so that the bioactive agent can interact with the additional component. Typically, the solution additive, and the additive-to-bioactive-agent ratio is selected to result in enhanced solubilizing and/or stabilizing of the bioactive agent in the resulting particle. In one aspect, the resulting particles have an amorphous morphology, and exhibit a glass transition temperature, or $T_g$, that is higher than that of the expected storage conditions. More particularly, an advantageous formulation of particle exhibits a glass transition temperature above about 50° C.

In another aspect, the resulting amorphous particles resist crystallization, for example even at relative humidity levels of 75% or higher. Alternatively, or in addition, the amorphous particles resist crystallization even at elevated temperatures.

The creation of specific particle morphologies by deposition may be selected by manipulating the solvent system used, by choosing the character of the surface of the delivery substrate, or both. For example, a delivery substrate may be selected so that the applied bioactive agent is encapsulated or entrained in interstitial spaces of the substrate, or delivery substrates may be selected so that such spaces are not available for the bioactive agent to engage. When a bioactive agent is at least partially encapsulated, relatively less surface area of the bioactive agent will be exposed, and therefore dissolution rate of the bioactive agent may be decreased. Therefore, a relatively porous substrate may be selected when slower dissolution rates are desired. Relatively high dissolution rates may also be facilitated by delivery substrates that are configured to minimize agglomeration by capturing the dots on or within the receiving substrate, though not necessarily encapsulating the dot.

The delivery substrate may exhibit a substantially impermeant surface, such that droplets deposited onto the substrate do not soak into the substrate, but rather evaporate from the substrate surface, leaving the bioactive agent on the substrate. The impermeant substrate may be selected to exhibit a smooth metallic or glass surface. The creation of amorphous microparticles may be facilitated by the use of a delivery substrate that is substantially nonpolar, or nonwettable, and nonporous to the solution applied. For example, a polytetrafluoroethylene substrate, such as TEFLON, or a substrate coated with paraffin, such as wax paper. It should be appreciated that a variety of nonpolar substrates are suitable for the preparation of amorphous microparticles. In one aspect, the delivery substrate and solution may be selected so that a droplet of applied solution exhibits a contact angle of less than about 90 degrees on the delivery substrate surface.

The choice of solvent may modify the effect of evaporation on a deposited drop of solution, which may in turn affect the morphology of the deposited bioactive agent. Assuming a nonporous delivery substrate, once a droplet is applied to the delivery substrate surface, solvent begins evaporating from the droplet. The evaporation typically results in toroidal flow patterns within the droplet itself, known as Marangoni convection patterns. These convection patterns may be generated due to surface tension gradients created along the droplet surface, which are in turn generated by the cooling effect of solvent evaporation. Concentration gradients may be formed as the solute dissolved within the droplet begins to concentrate due to solvent evaporation.

It should be appreciated that the gradual concentration of the deposited solution eventually results in precipitation of the bioactive agent as solvent is removed. Additionally, or in the alternative, where more than one solvent is present in the deposited droplet, evaporation may result in differential concentration of one solvent over the other, resulting in changes in the solubility of the dissolved medicament, and potentially permitting the formation of a desired particle morphology.

Additionally, the interaction of the solution with the surface of the delivery substrate may also effect the morphology of the deposited bioactive agent. For example, where the outermost edge (or contact line) of the drying droplet is effectively pinned in place by virtue of interaction with the delivery substrate, solvent evaporates from the edge of the droplet and is replenished by solvent from the interior of the droplet, resulting in transport of the dissolved solute to the edge. As a result, concentration patterns develop inside the droplet wherein a larger accumulation of precipitate occurs near the edge of the deposited droplet.

The formation of a "ring" of deposited material may occur in two phases. In the first phase, the contact angle of the droplet on the delivery substrate at the contact line may decrease, while the contact line itself holds its original position. The contact angle then continues to decrease with time, as the droplet volume decreases, increasing the concentration of the solute in the droplet. Precipitation may occur during this phase. However, when the contact angle decreases to a critical angle, a second phase of evaporation begins wherein the contact line recedes while the contact angle with the substrate remains constant. The rate of decrease of the contact angle in the first phase depends on the evaporation rate of the droplet. Additional precipitation may occur during this stage.

Where the deposited solution includes an additive, as discussed above, the interaction of the additive with both the solvent system and the bioactive agent should also be considered. For example, where the additive is a polymer, as the deposited droplet evaporates, the remaining solution becomes supersaturated with respect to both the polymer additive and the bioactive agent. The supersaturated system is an unstable system. This may result in a simple precipitation of the bioactive agent and the additive into small nanometer-sized aggregates or particles. However, the supersaturated condition may produce either a phase separation within the volume of the remaining droplet (a microemulsion or nanoemulsion) or a metastable phase system (also referred to as the "ouzo" effect). Because the polymer additive and bioactive agent typically prefer one of the solvent system components, they will typically precipitate or phase-separate together as a complex. The residual solvent may then continue to evaporate until the droplets are dried.

This evaporative process typically produces nanometer-scale particles. These nanoparticles are typically, single- or multiphase materials that appear to be a continuous phase. The bioactive agent is typically dispersed throughout the particle volume such that it has the greatest possible interaction with the solubilizing and stabilizing additive, producing a therapeutic substance with the advantages described above.

The particular solvents selected, the concentration of the desired solute, and the characteristics of the delivery substrate may therefore be selected so as to favor the formation of the target morphology within the deposited droplet. For example, the selected bioactive agent may be ejected or deposited as a solution in one or more solvents. Whereas for some bioactive agents, a single solvent will provide the necessary properties for formation of particles of the desired morphology, the bioactive agent is more typically deposited as a solution of two or more solvents. More typically, the solvent system used includes two or three solvents.

The solvents selected are typically completely miscible in some ratio, and may be miscible in any ratio. Generally the solvents are selected to exhibit a boiling point of around 90° C. or less, so that evaporation from the deposited droplet is reasonably efficient. The solvents should exhibit a dielectric constant less than that of water, and where more than one solvent is used in combination, the dielectric constant of at least two of the solvents should differ from each other. That is, one solvent should be more polar, and another should be less polar. The dielectric constant of the solvents used should fall between about 2 and about 40. Stated in another way, one solvent should be capable of yielding greater concentrations of the drug than any of the other solvent used in the solvent system. It is typically desirable to use solvents that are either substantially nontoxic, or that evaporate substantially completely to leave a substantially nontoxic residue.

Without wishing to be bound by theory, it is believed that proper selection of the solvent system permits differential evaporation of the solvents from a droplet in order to change the polarity of the solvent system. This evaporation may occur after the droplet is deposited onto the substrate, or may occur after formation of the droplet, and before the droplet reaches the substrate. The change the polarity of the solvent system may, result in precipitation of the bioactive agent from the droplet. The rate of change in droplet polarity may be modified by appropriate solvent selection.

The solvent system is typically selected so that the bioactive agent exhibits a differential solubility in at least two of the solvent components of the solvent system. For example, the solvent system may be selected to include at least one solvent having a low dielectric constant, and/or a low polarity, and/or a relatively low boiling point, and a second solvent with a relatively higher dielectric constant, higher polarity, and/or higher boiling point, among other physical characteristics. In one aspect the solvent system may include at least some water.

Selected solvents having a low dielectric constant, low polarity, and low boiling points include, without limitation, chloroform, tetrabromoethane, tetrachloroethylene, trichlorethylene, trichloroacetic acid, trichloroethane, 1,2-dichloroethane, trichloroethylene, bromoform, tetrahydrofuran, and toluene. Selected solvents having a higher relative dielectric constant, high polarity, and higher boiling points include, without limitation, alcohols having a boiling point less than 90° C. Particularly suitable alcohols include ethanol, propanol, isopropanol, butanol, and isobutanol.

The formation of amorphous microparticles may be facilitated by the use of a solvent system including a halocarbon solvent, and an alcohol solvent. For example, the solvent system may include an ethanol component and a chloroform component. A particularly advantageous solvent system for the formation of amorphous microparticles includes ethanol and chloroform in a ratio of between about 70:30 and 90:10 by volume, more particularly ethanol and chloroform in a ratio of about 80:20.

A desired morphology can be discovered through experimentation, in which one or more application parameters or delivery systems are varied until a desired particle morphology is achieved. For example, parameters affecting drop size, such as nozzle size and/or chamber size, can be varied. Furthermore, additional or alternative parameters, such as solution concentration, drop pattern, and/or drying temperatures can be varied. Test morphologies can be formed according to the set parameters. Such morphologies can be prepared with different parameter settings until a desired morphology is obtained. Once a desired morphology rate is achieved, the parameters used to make that morphology can be used to repeatedly and consistently prepare the bioactive agent in the target morphology.

Selected particle sizes, or amorphous or crystalline forms may have a strong effect on the bio-availability of selected medicaments. For example, medicament particles that are too small may result in too-rapid absorption of a medicament, leading to elevated levels in the subject. Alternatively, medicament particles that are too large may not dissolve sufficiently rapidly to give the desired bioavailability in combination with the method of delivery. The particular morphology and/or crystal structure of the deposited medicament may therefore be of some importance in the design of the medicament.

FIG. 9 is a flow chart showing an exemplary method, shown generally at 100, of preparing a desired morphology of a bioactive agent. Method 100 includes, at 102, selecting a target particle morphology for the bioactive agent. The method also includes, at 104, preparing a solution of the bioactive agent. The method further includes, at 106, applying the solution to a substrate to form particles having the target morphology. Such a method can be used to produce a particles of the bioactive agent having a target morphology, or at least a morphology substantially close to the target morphology.

FIG. 10 is a flow chart showing an alternative and exemplary method, shown generally at 200, of preparing a desired morphology of a bioactive agent. Method 200 includes, at 202, selecting a solvent system to produce a target particle morphology for the bioactive agent. The method also includes, at 204, preparing a solution of the bioactive agent in the selected solvent system. The method further includes, at 206, applying the solution to a substrate so as to form particles having the target morphology. The method may optionally further include, at 208, preparing a second solution of the bioactive agent, which may be the same or different than the first solution, and, at 210, applying the second solution to the previously formed particles, so that the particles act as seed particles.

In the method of FIG. 10, the second solution may be the same or different from the first solution. Additionally, the application of the second solution may result in larger particles having the target particle morphology, by increasing the size of the seed particles. Alternatively, the presence of the seed particles may generate additional particles having substantially the same morphology.

The above methods may be used to prepare a desired morphology of a variety of bioactive agents, particularly where the bioactive agent is a medicament. Nanoparticles of a variety of bioactive agents may be prepared via application of droplets of the bioactive agent to a substrate, including the drugs glyburide, digoxin, prednisolone, lovastatin, and indomethacin.

Glyburide, also known as glibenclamide, is a sulfonylurea oral hypoglycemic agent used in the management of diabetes. Glyburide contains a sulfonylurea core structure and a cyclohexyl ring substituent, and has a molecular weight of 494. Glyburide is a weak acid with a pKa of 5.3, and therefore exhibits a low aqueous solubility at acidic pH levels. The structure of glyburide is provided below:

It has been determined that a reduced bioavailability of glyburide is related to the particle size and particle size distribution. In particular, particles that are too small result in undesirably high glyburide blood levels, with an attendant increased risk of hypoglycemia, whereas particles that are too large cannot dissolve sufficiently rapidly for the entire administered dose to be available to the patient.

By manipulating application parameters, any or a combination of any of the following: the solvent system, the nature of the delivery substrate, the application system, and application parameters nanometer-scale particles of glyburide are produced. These nanoparticles appear to be substantially amorphous, and display a substantially narrow range of particle sizes. This morphology offers a substantial utility for improving the bioavailability of glyburide in patients with diabetes, and by similarly fine-tuning application parameters, similarly advantageous morphologies of other medicaments may be prepared.

Glyburide was dissolved in a solvent composition of ethanol:chloroform 80:20 by volume to a concentration of 5 mg/mL. The glyburide solution was deposited onto a polytetrafluoroethylene delivery substrate using a thermal ejection cartridge that produced droplets having drop weights of approximately 11 ng. The firing voltage was 13 volts, the pulse width was 0.5 microseconds, and the firing frequency was 5.0 KHz. These application parameters produced, upon evaporation of solvent, amorphous nanoparticles of glyburide that were substantially spherical.

The application of glyburide was repeated with a firing voltage of 5 volts, a pulse width of 4 microseconds, and a firing frequency of 5.0 KHz. These application parameters also produced amorphous microparticles. A range of sizes of substantially spherical particles was produced, with the smallest having a diameter of approximately 125 nm.

Glyburide was also applied to a wax paper substrate, keeping the remaining application parameters consistent. The application also yielded amorphous spherical microparticles.

Application of a 5 mg/mL 80:20 ethanol:chloroform solution of glyburide to a polytetrafluoroethylene and GRAS (Generally Recognized As Safe) substrate using a micropipette rather than a thermal ejection apparatus also resulted in the formation of amorphous spherical microparticles, although the average size of the microparticles was larger than those produced by thermal ejection.

Digoxin is one of a family of cardiac drugs that have specific effects on the myocardium. Digoxin typically occurs as odorless white crystals that melt with decomposition above 230° C. The drug is practically insoluble in water and in ether; slightly soluble in diluted (50%) alcohol and in chloroform; and freely soluble in pyridine. Digoxin has the structure provided below:

Digoxin was dissolved in a solvent composition of ethanol:chloroform 80:20 by volume to a concentration of 5 mg/mL. The digoxin solution was deposited onto a polytetrafluoroethylene delivery substrate using a thermal ejection cartridge that produced droplets having drop weights of approximately 11 ng. The firing voltage was 13 volts, the pulse width was 0.5 microseconds, and the firing frequency was 5.0 KHz. These application parameters produced, upon evaporation of solvent, amorphous spherical microparticles of digoxin. The majority of the microparticles had a diameter of between about 100 nm and about 600 nm.

It is presumed that pipetting or micropipetting the same solution composition onto a substrate of teflon and/or glass will also generate the formation of spherical nanoparticles.

Prednisolone is an adrenocortical steroid, that is typically a white crystalline powder. It is very slightly soluble in water, slightly soluble in alcohol, in chloroform, in dioxane, and in methanol. Prednisolone has the structure below:

Prednisolone was dissolved in a solvent composition of ethanol:chloroform 80:20 by volume to a concentration of 5 mg/mL. The prednisolone solution was deposited onto a polytetrafluoroethylene delivery substrate using a thermal ejection cartridge that produced droplets having drop weights of approximately 11 ng. The firing voltage was 13 volts, the pulse width was 0.5 microseconds, and the firing frequency was 5.0 KHz. These application parameters produced, upon evaporation of solvent, amorphous spherical microparticles of prednisolone. The majority of the microparticles had a diameter of less than about 1 µm, but were somewhat less defined than the microparticles produced using either glyburide or digoxin.

Lovastatin is a member of the family of HMG-CoA reductase inhibitors, or statins. Lovastatin has the structure below:

200 mg each of Lovastatin and a selected polymer additive were dissolved in a methanol solution and applied to a substrate. Three polymer additives were tested, LUTROL F127, polyvinylpyrrolidine (PVP), and HPMCAS-MF. In each case, solvent was removed under reduced pressure, and the resulting residue was dried further for 30 minutes in vacuo. The resulting material was collected by scraping, and the dissolution characteristics of the material were determined in 67 mM phosphate buffer containing 1% sodium lauryl sulfate, at pH 7.4 at a concentration of approximately 1,400 µg/mL.

For each composition including a polymer additive, the rate of dissolution of the composition in the aqueous buffer solution was significantly improved with respect to a composition of lovastatin alone.

In another example, solutions of lovastatin and a polymer additive were prepared in methanol by dissolving equal parts of the drug and a polymer to a final concentration of 20 mg solids/mL. The polymers used included LUTROL F127, PVP, and HPMCAS. The solutions were dispensed onto a polytetrafluoroethylene delivery substrate using a thermal ejection cartridge where the dispensing conditions included voltage=7.0 to 13.0 V, pulse width=0.5 to 2.75 µs, and a firing frequency of 200 Hz. These application parameters produced, upon evaporation of the solvent, amorphous drug-polymer particles that were substantially spherical.

Although the present disclosure has been provided with reference to the foregoing operational principles and embodiments, it will be apparent to those skilled in the art that various changes in form and detail may be made without departing from the spirit and scope defined in the appended claims. The present disclosure is intended to embrace all such alternatives, modifications and variances. Where the disclosure or claims recite "a," "a first," or "another" element, or the equivalent thereof, they should be interpreted to include one or more such elements, neither requiring nor excluding two or more such elements.

What is claimed is:

1. A method of preparing nanoparticles of a bioactive agent, comprising:
  selecting a solvent composition;

selecting a deposition substrate;

preparing a solution of the bioactive agent in the solvent composition; and applying the solution to the substrate as a plurality of droplets;

wherein evaporation of the applied solution on the substrate produces nanoparticles containing the bioactive agent; and wherein the bioactive agent is selected from the group consisting of glyburide, digoxin, prednisolone, lovastatin, and indomethacin.

2. The method of claim 1, wherein the solvent composition includes at least two solvent components.

3. The method of claim 2, wherein bioactive agent has a differential solubility in the at least two solvent components.

4. The method of claim 2, wherein the two solvent components each have a dielectric constant between about 2 and about 40, and each have a boiling point below 90° C.

5. The method of claim 1, wherein the solution includes at least one solvent selected from the group consisting of chloroform, tetrabromoethane, tetrachloroethylene, trichlorethylene, trichloroacetic acid, trichloroethane, 1,2-dichloroethane, trichloroethylene, bromoform, tetrahydrofuran, and toluene; and at least one solvent selected from the group consisting of ethanol, propanol, isopropanol, butanol, and isobutanol.

6. The method of claim 1, wherein the solvent composition includes ethanol and chloroform.

7. The method of claim 6, wherein the solvent composition includes ethanol and chloroform in a ratio of about 80:20.

8. The method of claim 1, wherein the solvent composition includes ethanol and chloroform in a ratio of between about 70:30 and 90:10.

9. The method of claim 1, wherein the substrate is selected to have a substantially nonpolar surface character.

10. The method of claim 9, wherein the substrate includes a fluorinated polymer.

11. The method of claim 9, wherein the deposition substrate includes paraffin.

12. The method of claim 1, wherein the substrate is selected to have a substantially impermeant surface character.

13. The method of claim 1, wherein applying the solution to the substrate includes ejecting droplets of the solution with a thermal ejection element.

14. The method of claim 1, wherein applying the solution to the substrate includes ejecting droplets of a glyburide solution with a piezoelectric ejection element.

15. The method of claim 1, wherein the solution includes at least one additive.

16. The method of claim 15, wherein the additive is a polymer additive.

17. The method of claim 1, wherein the resulting nanoparticles are substantially amorphous.

18. The method of claim 1, wherein the resulting particles are substantially spherical.

19. The method of claim 1, wherein the particles have an average size of less than about 1 µm.

20. The method of claim 1, wherein the bioactive agent is glyburide.

21. The method of claim 1, wherein the bioactive agent is digoxin.

22. The method of claim 1, wherein the bioactive agent is prednisolone.

23. A method of preparing amorphous nanoparticles of a bioactive agent, the method comprising:

preparing a solution of a bioactive agent that is glyburide, digoxin, prednisolone, lovastatin, or indomethacin in a composition of ethanol and chloroform; and applying the solution to a substantially impermeant substrate as a plurality of droplets;

wherein evaporation of the applied bioactive agent solution produces at least substantially amorphous nanoparticles of the bioactive agent.

24. The method of claim 23, wherein the solution includes a polymer additive.

* * * * *